United States Patent [19]

Strong

[11] 4,035,471
[45] July 12, 1977

[54] HYDROGEN PEROXIDE STABILIZATION WITH CYANOALKYL ETHERS OF TRIALKANOLAMINES

[75] Inventor: Walker Albert Strong, Wadsworth, Ohio

[73] Assignee: PPG Industries, Inc., Pittsburgh, Pa.

[21] Appl. No.: 694,502

[22] Filed: June 10, 1976

[51] Int. Cl.$^2$ .................................... C01B 15/02
[52] U.S. Cl. .............................. 423/272; 423/584
[58] Field of Search ........... 423/272, 584; 252/186; 260/465.5 R

[56] References Cited

U.S. PATENT DOCUMENTS

| 3,402,128 | 9/1968 | Puchta et al. | 423/272 |
| 3,775,333 | 11/1973 | Loffelman et al. | 423/272 |
| 3,947,374 | 3/1976 | Loffelman et al. | 423/272 |

Primary Examiner—O. R. Vertiz
Assistant Examiner—Wayne A. Langel
Attorney, Agent, or Firm—William M. Dooley

[57] ABSTRACT

Aqueous hydrogen peroxide solutions are stabilized with the use of cyanoalkyl ethers of trialkanolamines, such as the condensation product of triethanolamine and acrylonitrile, preferably in combination with known stabilizer additives, i.e., stannates, nitrates, and pyrophosphates.

8 Claims, No Drawings

HYDROGEN PEROXIDE STABILIZATION WITH CYANOALKYL ETHERS OF TRIALKANOLAMINES

BACKGROUND OF THE INVENTION

This invention relates to retarding the decomposition of hydrogen peroxide in aqueous solution.

Dilute aqueous hydrogen peroxide in concentrations of between about 3 and 10 weight percent has many uses, including bleaching, hair dyeing and waving, processing of photographs for permanence, and preparation of cosmetics and mild antiseptics.

Hydrogen peroxide is commonly sold in concentrated aqueous solutions of between about 30 and 90 weight percent, which are often diluted by the purchaser for use or sale. The concentrated solutions are quite stable when pure, but contaminants which promote decomposition may be introduced in storage and handling. The common use of tap water for dilution of the concentrate may introduce significant quantities of decomposition-inducing cations such as iron, copper, and manganese cations. If diluted solutions are stored rather than used immediately, substantial decomposition may occur.

Numerous organic and inorganic stabilizers for aqueous hydrogen peroxide are known. Various combinations of stannate, nitrate, orthophosphate, and pyrophosphate ions for use at varying pH have been proposed. See, for example, U.S. Pat. Nos. 3,701,825, 3,373,113, 3,591,341, and 3,607,053. U.S. Pat. No. 3,781,409 discloses the use of water-soluble tin compounds, preferably in conjunction with organic complexing agents such as organic phosphonic acids, 8-hydroxyquinoline, hydroquinone, nitrilo triacetic acid, alkyl phenols, and phosphate esters.

It has now been found that decomposition of aqueous hydrogen peroxide solutions may be treated by dissolving therein a minor stabilizing concentration of cyanoalkyl ethers of trialkanolamines.

The cyanoalkyl ether may be used alone or, preferably, in combination with known stabilizing additives, notably stannates, or more preferably, in combination with stannates, nitrates, and pyrophosphates.

DETAILED DESCRIPTION OF THE INVENTION

In accordance with this invention, a stabilized aqueous hydrogen peroxide solution is prepared having dissolved therein a minor stabilizing amount of a soluble cyanoalkyl ether of a trialkanolamine.

Useful soluble cyanoalkyl ethers may be represented by the general formula

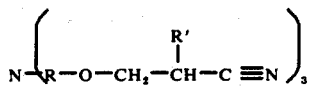

wherein each R independently is a lower alkylene group having 1 to 4 carbons, such as methylene, ethylene, propylene, and tetramethylene, and each R' independently is hydrogen or a methyl group.

A method useful for preparing the comtemplated cyanoalkyl ethers is described in U.S. Pat. No. 2,326,721, particularly Examples 6 and 7. Briefly, the cyanoalkyl ethers may be prepared by reaction of a trialkanolamine such as triethanolamine or triisopropanolamine with acrylonitrile or methacrylonitrile in the presence of an alkali metal alkylate such as sodium methylate or potassium ethylate.

Non-symmetrical cyanoalkyl ethers may be obtained by the same method starting with a non-symmetrical trialkanolamine such as diethanolmethanolamine, or by reacting a symmetrical or non-symmetrical trialkanolamine with a mixture of acrylonitrile and methacrylonitrile. The resulting non-symmetrical cyanoalkyl ethers and mixtures thereof are also expected to be useful in the practice of this invention.

The stabilizing cyanoethyl ethers of trialkanolamines herein contemplated may be included in widely varying concentrations in aqueous hydrogen peroxide solutions of any substantial concentration to retard the decomposition of the hydrogen peroxide, particularly to retard decomposition induced by polyvalent metal cation contaminants. The preferred stabilizer concentration depends upon the amount of contamination anticipated. Where a hydrogen peroxide solution is to be stabilized, for example, against contaminant cations introduced in handling or by dilution with tap water, a useful stabilizing concentration of a cyanoethyl ether of a trialkanolamine usually will be from about 0.01 to about 2.0 weight percent, more preferably from about 0.05 to about 0.5 weight percent, by weight of hydrogen peroxide. Amounts of more than about 2.0 weight percent may be used, but do not appear to have advantage over lower amounts, and excessive amounts of stabilizer may be less effective than preferred amounts.

Stabilized hydrogen peroxide solutions of any substantial hydrogen peroxide concentration may be prepared. Thus, aqueous hydrogen peroxide solutions of between about 3 and 90 weight percent hydrogen peroxide may be stabilized in accordance with this invention. Especially useful are about 30 to 70 weight percent solutions, which may be shipped conveniently and then diluted by the user to a desired concentration, typically about 3 to 10 weight percent.

The stabilized solutions are kept acidic, having a pH usually between about 1 and 6, preferably between about 1 and 4.5, as measured with a glass electrode, depending upon the concentration of hydrogen peroxide. If the stabilized solution is dilute, i.e., between about 3 and 10 weight percent, especially if the dilute solution is to be stored for a time, it is desirable to adjust the pH to between about 3 and 4.5. More concentrated solutions usually have a lower pH. For example, a 30 weight percent solution will usually have a pH of about 2.5 to 3. A 70 weight percent solution may have a pH of 1 or even lower. The pH of a stabilized solution may be lowered by the addition of orthophosphoric acid, nitric acid, or another organic or inorganic acid inert to hydrogen peroxide. The pH may be raised by the addition of sodium hydroxide, sodium carbonate, trisodium phosphate, or another alkaline material inert to hydrogen peroxide.

It is highly preferred to use the stabilizers of this invention in combination with stannate compounds in stabilized aqueous hydrogen peroxide. More preferably, the stabilizers are used in combination with stannates, nitrates, and inorganic phosphates.

Useful stannate compounds include ammonium and alkali metal stannates such as sodium stannate, potassium stannate, and ammonium stannate. Sodium stannate trihydrate is preferred. The stannate compound may be used in an amount of between about 0.001 and 1.0 weight percent or more (calculated as sodium stannate trihydrate), usually between about 0.01 and 0.5 weight percent by weight of hydrogen peroxide. When a stannate compound is used, it should be added to the hydrogen peroxide solution before other additives in order to avoid difficulty in dissolving the stannate.

The presence of nitrate ion in aqueous hydrogen peroxide solution inhibits corrosion of the aluminum vessels in which the solutions are manufactured and stored. Sources of nitrate ion include nitric acid, alkali metal nitrates such as sodium nitrate, and ammonium nitrate. The amount of nitrate used may be between about 0.001 and 1.0 weight percent or more (calculated as ammonium nitrate), usually between about 0.01 and 0.5 weight percent, by weight of hydrogen peroxide.

Inorganic phosphate, i.e., orthophosphate or, preferably, pyrophosphate, may also be included to further increase the stability of hydrogen peroxide solutions stabilized according to this invention. Sources of inorganic phosphate include orthophosphoric acid, pyrophosphoric acid, and their alkali metal and ammonium salts, such as disodium hydrogen phosphate, disodium dihydrogen pyrophosphate, tetrasodium pyrophosphate, and ammonium dihydrogen phosphate. The inorganic phosphate may be used in amounts of between about 0.001 and 2.0 weight percent or more (calculated as disodium dihydrogen pyrophosphate), preferably between about 0.005 and 0.75 weight percent by weight of hydrogen peroxide. Pyrophosphate is preferred.

Especially desirable stabilized aqueous hydrogen peroxide solutions have dissolved therein between about 0.025 and 0.35 weight percent of stabilizing cyanoalkyl ether of a trialkanolamine, between about 0.05 and 0.08 weight percent nitrate calculated as ammonium nitrate, between about 0.12 and 0.16 weight percent stannate calculated as sodium stannate trihydrate, and between about 0.10 and 0.18 weight percent pyrophosphate calculated as disodium dihydrogen pyrophosphate, at a pH of between about 3.0 and 1.0, and hydrogen peroxide concentrations of between about 30 and 70 weight percent. The additive concentrations are by weight of hydrogen peroxide.

The stabilizer compounds of this invention may be added directly to the aqueous hydrogen peroxide to be stabilized, or they may first be dissolved in water or aqueous hydrogen peroxide either alone or together with other additives.

EXAMPLE

A five cation contaminant solution was prepared from aqueous solutions of $AlK(SO_4)_2 \cdot 12H_2O$, $FeNH_4(SO_4)_2$, $CuSO_4$, $MnSO_4$, and $K_2CrO_4$. In each case when it was used, sufficient of this solution was added to a 6 weight percent hydrogen peroxide test solution to provide the following concentrations of ions in each such test solution:

$Al^{+++}$: 0.25 milligrams/liter
$Fe^{+++}$: 0.25 milligrams/liter
$Cu^{++}$: 0.05 milligrams/liter
$Mn^{++}$: 0.025 milligrams/liter
$Cr^{++++++}$: 0.012 milligrams/liter Stability of tested solutions was measured by the $S_{100}$ test. This test is performed by placing a weighed sample of test solution, about 45 milliliters, in a 50 milliliter volumetric-type flask having an extra-long neck. (The flask is passivated overnight with 35 percent nitric acid before use.) The body of the flask is then immersed up to the neck in water at 100° C. for 24 hours, with the mouth of the flask lightly covered but not sealed. The flask neck, which extends above the heat bath, serves as a condenser to minimize loss of water from the test solution. After 24 hours, the weight of test solution remaining in the flask is determined and expressed as a percentage of the initial weight. This percentage is the $S_{100}$ value. A high $S_{100}$ value corresponds to a low loss of oxygen from the solution and therefore to high stability of the hydrogen peroxide.

An aqueous 35 weight percent hydrogen peroxide solution was prepared containing 0.28 percent $N(CH_2CH_2-O-CH_2CH_2-C \equiv N)_3$, 0.14 percent sodium stannate trihydrate, 0.064 percent ammonium nitrate, and 0.14 percent disodium dihydrogen pyrophosphate. The amounts of the stabilizer ingredients are given in weight percent by weight of hydrogen peroxide. A portion of the solution was diluted to 6 weight percent hydrogen peroxide and the pH adjusted to 3.5. A portion of the 6 weight percent solution was treated with the cation contaminant solution and then was tested for stability. An $S_{100}$ value of 92.2 percent was measured.

Two 6 weight percent hydrogen peroxide reference formulations were prepared and tested as above, except that the $N(CH_2CH_2-O-CH_2CH_2-C \equiv N)_3$ was omitted. $S_{100}$ values of 82.7 and 75.2 were measured.

The results of this experiment show the desirable retarding effect which a cyanoethyl ether of triethanolamine has on the decomposition of aqueous hydrogen peroxide.

Similarly, it is expected that the other cyanoalkyl ethers of trialkanolamines disclosed herein would also show a useful retarding effect when used in accordance with this invention.

Although this invention has been described with reference to particular details, experiments, and preferred embodiments, the particulars of the description are not intended to limit the scope of the invention except insofar as they appear in the following claims.

I claim:

1. A stabilized aqueous hydrogen peroxide solution having between about 3 and 90 weight percent hydrogen peroxide, having dissolved therein a minor stabilizing concentration of a cyanoalkyl ether represented by the general formula

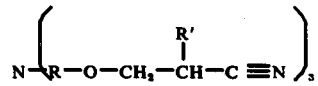

wherein each R independently is a lower alkylene group having 1 to 4 carbons and each R' independently or methyl.

2. The hydrogen peroxide solution of claim 1 having dissolved therein between about 0.01 and 2.0 weight percent, by wieght of hydrogen peroxide, of the cyanoalkyl ether, between about 0.001 and 1.0 weight percent, calculated as sodium stannate trihydrate, of an alkali metal or ammonium stannate and between about 0.001 and 1.0 weight percent, calculated as ammonium nitrate, of nitric acid or an alkali metal or ammonium nitrate.

3. The hydrogen peroxide solution of claim 2 further having dissolved therein between about 0.001 and 2.0 weight percent, calculated as disodium dihydrogen pyrophosphate, of pyrophosphoric acid or an alkali metal or ammonium pyrophosphate.

4. The hydrogen peroxide solution of claim 1, wherein the cyanoalkyl ether is the compound by the formula N(CH$_2$CH$_2$—O—CH$_2$CH$_2$—C≡N)$_3$.

5. A method of stabilizing aqueous hydrogen peroxide, which comprises adding to a 3 to 90 weight percent aqueous hydrogen peroxide solution a minor stabilizing amount of a cyanoalkyl either represented by the general formula

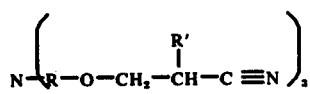

wherein R independently is a lower alkylene group having 1 to 4 carbons and each R' independently is hydrogen or methyl.

6. The method of claim 5 which further comprises adding between about 0.01 and 2.0 weight percent, by weight of hydrogen peroxide, of the cyanoalkyl ether, between about 0.001 and 1.0 weight percent, calculated as sodium stannate trihydrate, of an alkali metal or ammonium stannate and between about 0.001 and 1.0 weight percent, calculated as ammonium nitrate, of nitric acid or an alkali metal or ammonium nitrate.

7. The method of claim 6 which further comprises adding between about 0.001 and 2.0 weight percent, calculated as disodium dihydrogen pyrophosphate, of pyrophosphoric acid or an alkali metal or ammonium pyrophosphate.

8. The method of claim 5, wherein the cyanoalkyl ether is the compound represented by the formula N(CH$_2$CH$_2$—O—CH$_2$CH$_2$—C≡N)$_3$.

* * * * *

UNITED STATES PATENT AND TRADEMARK OFFICE
CERTIFICATE OF CORRECTION

PATENT NO. : 4,035,471
DATED : July 12, 1977
INVENTOR(S) : Walker Albert Strong

It is certified that error appears in the above-identified patent and that said Letters Patent are hereby corrected as shown below:

Column 4, line 56, before "or methyl" insert --is hydrogen--.

Column 4, line 59, "wieght" should be --weight--.

Column 5, line 4, after "compound" insert --represented--.

Signed and Sealed this

Twenty-fourth Day of January 1978

[SEAL]

Attest:

RUTH C. MASON
*Attesting Officer*

LUTRELLE F. PARKER
*Acting Commissioner of Patents and Trademarks*